United States Patent [19]

Weiss et al.

[11] 4,394,063
[45] Jul. 19, 1983

[54] DEVICE FOR RECONSTRUCTING LAYER IMAGES OF A THREE-DIMENSIONAL OBJECT BY MEANS OF AN ADJUSTABLE IMAGING MATRIX

[75] Inventors: Hermann Weiss, Hamburg; Erhard Klotz, Halstenbek; Horst Peemöller, Hamburg; Rolf Linde, Haseldorf; Wilfried Mauser, Hamburg, all of Fed. Rep. of Germany

[73] Assignee: U.S. Philips Corporation, New York, NY

[21] Appl. No.: 207,325

[22] Filed: Nov. 17, 1980

[30] Foreign Application Priority Data

Nov. 17, 1979 [DE] Fed. Rep. of Germany ....... 2946442

[51] Int. Cl.³ .................... G02B 5/32; G03H 1/28; A61B 6/02
[52] U.S. Cl. ........................ 350/162.13; 350/3.75; 350/247
[58] Field of Search ........ 350/162.13, 3.67, 3.75–3.79, 350/3.81, 3.85, 3.86, 247, 254, 3.73

[56] References Cited

U.S. PATENT DOCUMENTS 3,765,741 10/1973 Kimura et al. ..................... 350/3.76
3,788,726 1/1974 Groh et al. ......................... 350/3.76
4,023,037 5/1977 Weiss et al. ....................... 350/3.73
4,078,177 3/1978 Tiemens ............................ 350/3.77

FOREIGN PATENT DOCUMENTS 2746035 4/1979 Fed. Rep. of Germany.

Primary Examiner—Bruce Y. Arnold
Attorney, Agent, or Firm—Marc D. Schechter

[57] ABSTRACT

A device for imaging layers of the interior of a three-dimensional object. The object is irradiated from a large number of radiation source positions which are distributed in one plane from this, a coded image of the object which coded image consists of separate perspective images is produced. The coded image is illuminated and imaged by means of an imaging matrix whose imaging elements are distributed in the matrix plane according to the flat distribution of the radiation source positions. Layer images of the object are formed on a photosensitive element by the superposition of the perspective images. For forming different layer images of the object, the imaging elements are positioned in different distributions of changed scale with respect to the distribution of the radiation source positions.

8 Claims, 7 Drawing Figures

DEVICE FOR RECONSTRUCTING LAYER IMAGES OF A THREE-DIMENSIONAL OBJECT BY MEANS OF AN ADJUSTABLE IMAGING MATRIX

BACKGROUND OF THE INVENTION

The invention relates to a device for producing images of layers of the interior of a three-dimensional object. A coded image is produced by irradiating the object from a large number of radiation source positions which are situated in one plane. The coded image consists of separate perspective images. Layer images of the object are formed from the coded image by superposition of the perspective images on a photosensitive element. The perspective images are superposed by means of an imaging matrix whose imaging elements are distributed in the matrix plane according to the flat distribution of the radiation source positions.

A device of this kind is known from German Offenlegungsschrift No. 27 46 035. In this Offenlegungsschrift, all perspective images of the coded image are superposed by means of a lens matrix which serves as an imaging matrix. In an image space of the lens matrix there is obtained a three-dimensional brightness distribution which corresponds to the density distribution in the three-dimensional object. When a photosensitive layer, for example, a frosted glass plate, is introduced into this superposition zone, images can be formed of arbitrary layers of the object, also oblique layers, by corresponding positioning or displacement of the radiation sensitive element.

It is a drawback of this method, however, that layers of the object are sharply imaged only if the photosensitive layer is situated within the depth of focus range of the lenses of the lens matrix. Because the depth of focus range of the lenses is limited, only a comparatively small part of the object can be reproduced by sharp layer images in the case of a large reconstructed object volume. Layer images of the object which are situated outside the depth of focus range are blurred. The depth of focus range can be increased by means of diaphragms in front of the lenses, but this causes a loss of brightness.

It is a further drawback of the known decoding device that it produces different layer images in different scales, so that diagnosis of the object on the basis of the layer images is impeded.

German Offenlegungsschrift No. 24 14 322 (corresponding to U.S. Pat. No. 4,023,037) discloses a holographic method for the reconstructing of layer images. In this method, the coded image is irradiated by means of a converging incoherent radiation beam. An image is then formed by combining the coded image, or a superposition of the perspective images, and a hologram which is arranged in the focal plane of a lens. The hologram serves as an imaging matrix in which the radiation source positions of the recording device are stored at a changed scale. For reconstructing different layer images, the coded image is displaced in the radiation beam in the direction of the optical axis. Different layer images of the objects are then reconstructed with different enlargements with respect to each other or with respect to the actual object layers and in different planes.

SUMMARY OF THE INVENTION

It is an object of the invention to provide a device for making sharp layer images of an object at the same scale where neither the photosensitive element nor the coded image has to be displaced for forming a set of parallel layer images.

To this end, in a device according to the invention different layer images of the object are formed by adapting the distribution of the imaging elements to the distribution of the radiation source positions.

In this device for the formation of layer images, the coded image, the imaging matrix and the photosensitive element are permanently positioned with respect to each other. By varying of the distribution of the imaging elements in the matrix plane, the individual perspective images of the coded image are superposed to varying extents, so that different layer images can be formed on the photosensitive element.

In a preferred embodiment according to the invention, the imaging elements are lenses which are displaceable in the matrix plane. Alternatively, the imaging matrices may be exchangeable, with different distributions of imaging elements on each matrix.

In a further preferred embodiment according to the invention, different layer images of the object are formed by using different holograms which serve as imaging matrices and in which the imaging elements are points of a point image. The distances between these points correspond to the distances between the radiation source positions, i.e. the radiation source positions are stored in different holograms at different scales.

DESCRIPTION OF THE PREFERRED EMBODIMENTS

Figure 1:
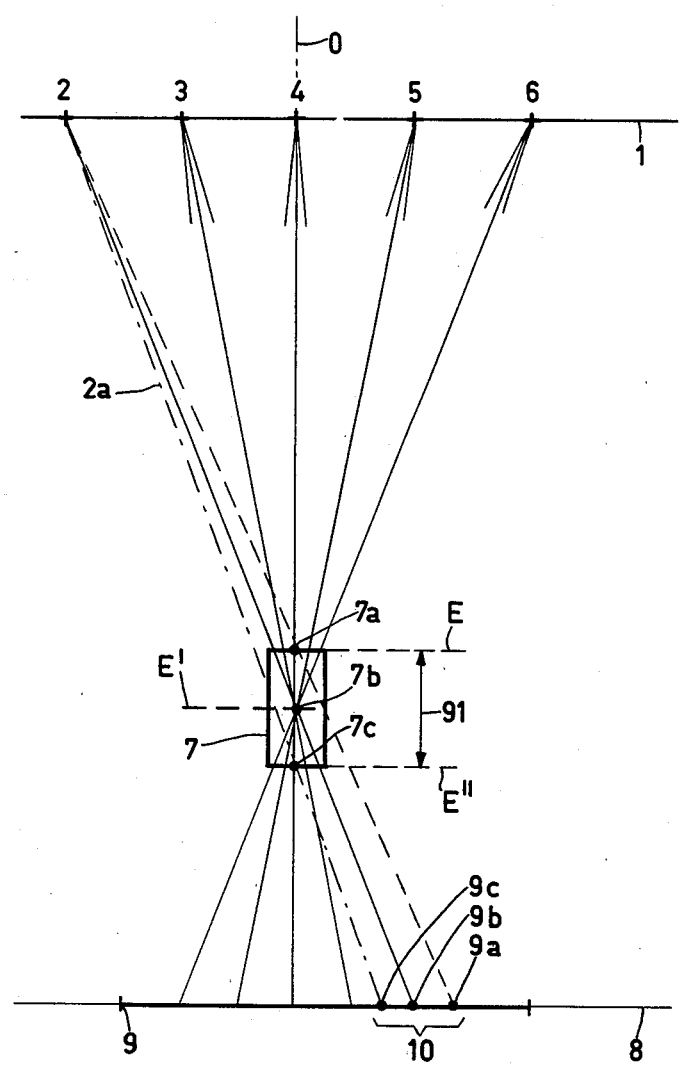
FIG. 1 shows a device for recording coded images of an object.

FIG. 1 shows a known fast tomosynthesis apparatus. It consists, for example, of several X-ray tubes 2 to 6 which are arranged in a radiation source plane 1. In operation an object 7 is irradiated by X-rays from the tubes from different perspectives in order to record an image 9 which is situated in a recording plane 8. Image 9 consists of several perspective images.

Alternatively only one X-ray tube may be used. In this case, the one tube is successively arranged at the positions of the X-ray tubes 2 to 6 and is flashed at each position.

The object 7 has a depth dimension perpendicular to the plane of FIG. 1 (the object table accomodating the object is not shown) across which the object 7 is to be recorded and decoded at a later stage or represented in individual layer images.

The X-ray tube 2, which emits a radiation beam 2a, images the individual points 7a, 7b, and 7c of the object 7. The points are situated, for example, on an optical axis 0 which extends perpendicular to the radiation source plane 1. Beam 2a images these points onto recording plane 8, for example, a film, so that the image points 9a, 9b, and 9c are produced thereon. The overall image produced by the radiation beam 2a represents a perspective image 10 of the object 7 which is a part of the coded image 9.

These image points 9a, 9b, and 9c together with the image points (not shown) produced by the other X-ray tubes 3 to 6, may also be considered to be point images of the radiation source distribution. A different point image is then associated with each object plane E, E' and E" which extends parallel to the radiation source plane 1. However, the individual point images all correspond to the flat distribution of the radiation source positions and differ only as regards the scale. It will be clear that, as the distance between the individual object planes E, E', E" and the recording plane 8 increases, the individual point images 9a, 9b, and 9c shift toward the edge of the coded image 9a. The point image for the object plane E, therefore, is larger than the point image 9c for the object plane E". The distance between the points 9a and 9c indicates the range in which the size of the individual point images varies.

When the coded image 9a is decoded in order to form a given layer image of the object 7, for example a layer image of the object plane E', use is made of an imaging matrix (11 in FIG. 2) whose imaging elements (12 in FIG. 2) are distributed in proportion to the positions of the image points 9a. Depending on the imaging scale of the layer image, the imaging matrix scale may be reduced with respect to the point image of the radiation source distribution. The layer image is then formed on a photosensitive element which is arranged at a fixed distance from the imaging matrix.

If the object layer situated in the object plane E" is to be imaged on the same photosensitive element at the same area, an imaging matrix must be used whose imaging elements are distributed in proportion to image points 9a at the positions of the image points 9c.

Figure 2:
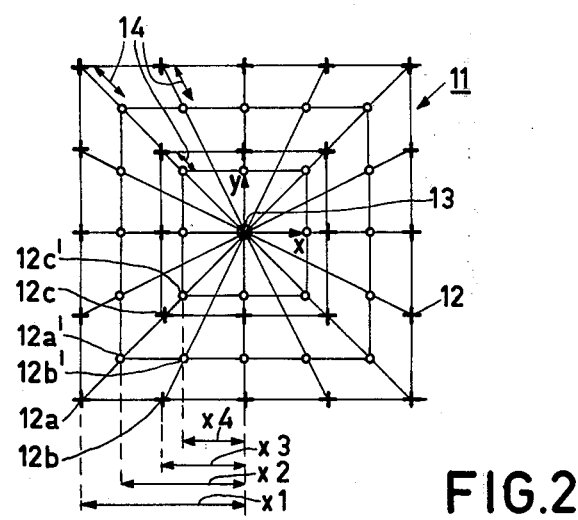
FIG. 2 shows an imaging matrix, the imaging elements of which are arranged according to different point images.

FIG. 2 shows a plan view of an imaging matrix 11 which comprises twenty-five imaging elements 12 which are arranged in the form of a matrix according to the distribution of the radiation source positions. The positions denoted by crosses (+) are associated, for example, with the point image of the object plane E according to FIG. 1, or with the object point 7a or the image point 9a thereof, whilst the positions denoted by circles (0) are associated, for example, with the object plane E" shown in FIG. 1, or with the object point 7c or the image point 9c thereof. The coordinate zero point 13 of the imaging matrix 11 belongs to both object planes E and E" (and also to plane E').

For varying of the imaging elements 12 according to the various point images, they can be displaced, for example, radially with respect to the center 13 in the direction of the arrows 14. Obviously, the complete imaging matrix can also be replaced by another matrix, the imaging elements of which are arranged according to the desired point image. The coordinates X1 and X3 of the imaging elements 12a, 12b, and 12c, and the coordinates X2 and X4 of the displaced imaging elements 12a', 12b', 12c' will always satisfy the rule X1:X3=X2:X4. In this example, the individual imaging elements 12 of the imaging matrix 11 are arranged in a grid having a constant grid dimension in the X-direction and the Y-direction of the rectangular coordinate system X, Y. The coordinates of the imaging elements in the X direction relate as, for example, X1:X3=X2:X4=2:1. This ratio is also applicable to displacements in the radial and in the Y direction for all imaging elements 12.

Figure 3:
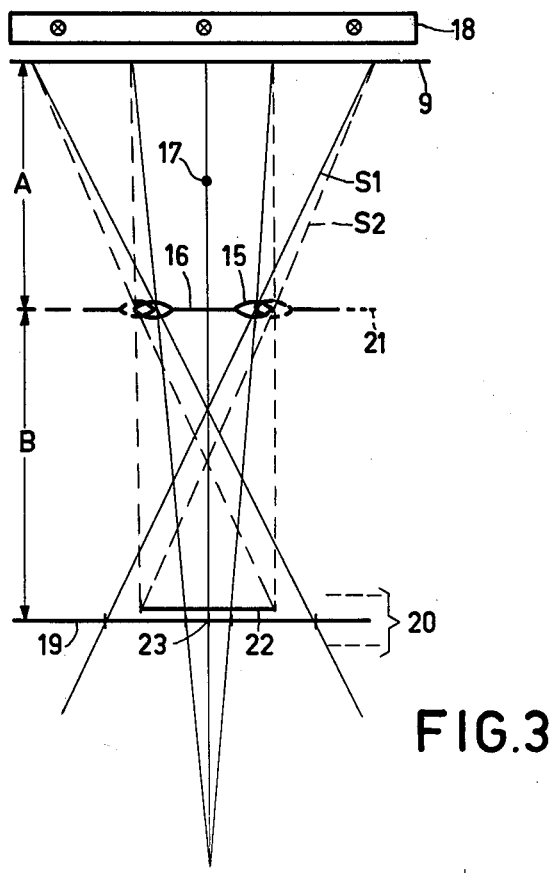
FIG. 3 shows a decoding device comprising a lens matrix and displaceable lenses.

The individual imaging elements 12 of imaging (decoding) matrix 11 can be, for example, lenses 15. FIG. 3 shows such a decoding device. This device comprises, for example, a lens matrix 16 which comprises lenses 15. Lens matrix 16 is arranged parallel to the coded image 9 and perpendicular to the optical axis 17 which extends perpendicular to the coded image 9 and which corresponds to the optical axis 0 in FIG. 1.

For illuminating the coded image 9 there is provided a light box 18. On the other side of the lens matrix 16 there is provided a photosensitive element 19, for example a frosted glass plate, a film or an image pick-up tube, on which the individual layer images of the object 7 can be formed.

The distance A between the coded image 9 and the lens matrix 16 and also the mean distance B between the lens matrix 16 and the photosensitive element 19 are constant. The photosensitive element 19, however, can be tilted or pivoted, for example, in the depth of focus range 20 of the lenses 15, in order to obtain oblique layer images which do not extend parallel to the lens matrix 16. To this end, the photosensitive element is suspended, for example, from gimbals. The lenses 15 are arranged to be displaceable in the matrix plane 21. Different distributions of the lenses 15 (beam paths S1, S2) thus produce layer images 22 and 23 which represent different layers of the object (shown in different planes for the sake of clarity).

Figure 4:
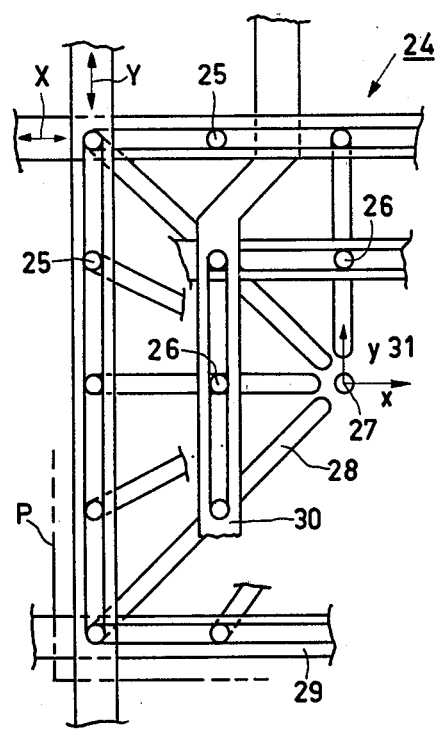
FIGS. 4 to 6 show special lens matrices comprising displaceable lenses.

A special embodiment of a lens matrix 24 in which the lenses or objectives consisting of several lenses can be displaced is shown in FIG. 4. Details such as springs, bearings, screws etc., however, are not shown.

The lens matrix 24 corresponds to the lens matrix 11 of FIG. 2. The outer lenses 25 and the inner lenses 26 can be displaced in slots 28, extending radially with respect to the center 27 (the zero point of the coordinate system X,Y) of the lens matrix 24. Displacement is in a plate P with guide/displacement strips 29, 30 in the X or the Y direction of the coordinate system X,Y, either by hand or by means of electromechanical adjusting members (arrows X,Y). In the coordinate center there is also arranged a lens 31, which, however, is arranged to be stationary. Displacement is performed simultaneously for all lenses 25 and 26 so that the coded images 9 can be continuously decoded. The displacement path for the inner lenses 26 amounts to only half the path for the outer lenses 25.

Figure 5:
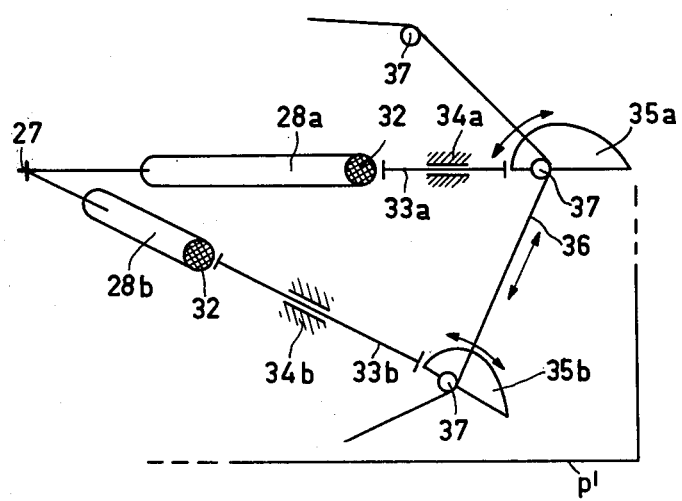

FIG. 5 shows a further device for displacing the lenses in the matrix plane. Lenses 32 are displaced in slots 28a and 28b extending radially with respect to the center 27, in a flat plate P' by means of mechanical rod systems 33a and 33b. The rod systems which are guided in bearings 34a and 34b and which are moved by means of cam discs 35a and 35b. The cam discs are driven by a common drive, for example a toothed belt 36. The toothed belt 36 is guided over gearwheels 37 which are rigidly connected to the cam discs 35a and 35b is driven either by hand or electrically.

Figure 6:
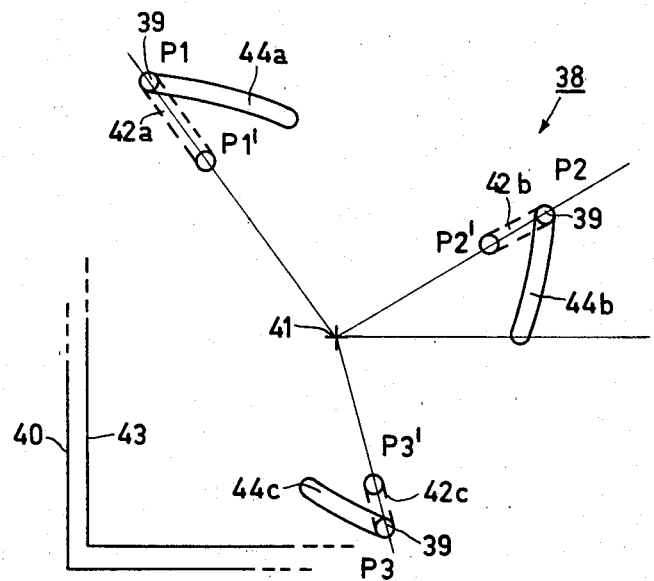

FIG. 6 shows a further embodiment of a lens matrix 38 comprising displaceable lenses 39. The lens matrix 38 consists of a flat first plate 40 which has guide slots 42a–42c which extend radially with respect to the center 41 of the lens matrix 38 and in which the lenses 39 are arranged. On the first plate 40 there is arranged a second plate 43 which has guide slots 44a–44c for the lenses 39; these slots extend helically with respect to the center 41. When the plates 40 and 43 are rotated with respect to each other around an axis which extends perpendicular to the plane of the plate and through the center 41, the lenses 39 can be displaced radially from their original positions P1, P2, P3 to the positions P1', P2', P3'. To this end, the lenses 39 may include elements which engage both guide slots 42 and 44.

However, the slots in the second plate 43 may alternatively be straight. In that case plates 40 and 43 are linearly displaced with respect to each other in order to displace the lenses 39.

Figure 7:
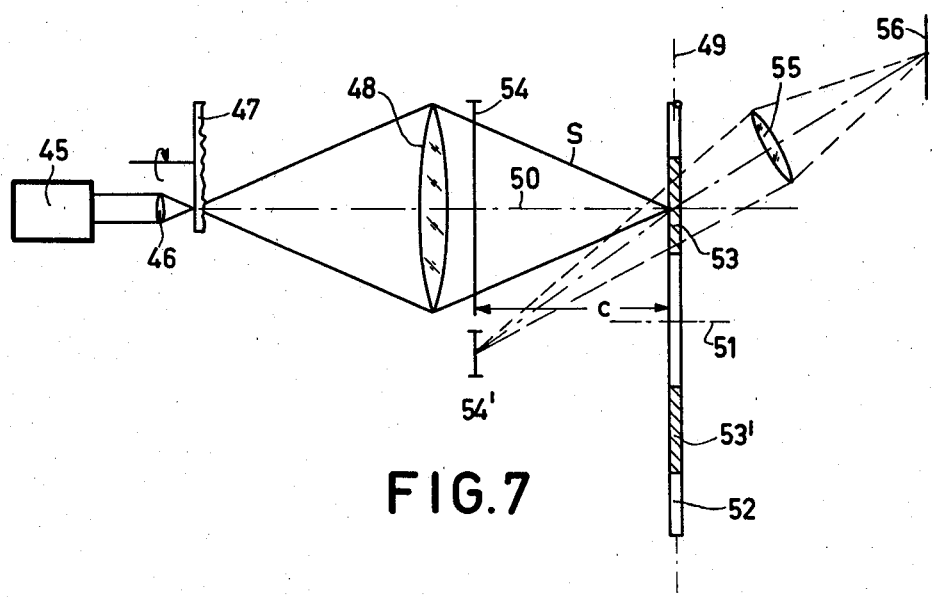
FIG. 7 shows a decoding device with several exchangeable holograms.

Different layer images can also be derived from a coded image by means of a holographic method. A method and a device of this kind are already known from German Offenlegungsschrift No. 24 14 322. FIG. 7 shows an improved device. A lens 46 which focuses a beam of a laser 45 forms a point light source. In the focus of the lens 46 there is arranged a rotating frosted glass plate 47 which disturbs or strongly reduces the spatial coherence of the laser light. A collecting lens 48 images the point light source in its focal plane 49 in which there is arranged a carrier disc 52 which rotates around an axis 51 which extends parallel to the optical axis 50 of the imaging system. On the carrier disc 52 there are provided several holograms 53 and 53' in which different point images for decoding the coded image 54 are stored. The coded image is arranged at a fixed distance C from the carrier disc 52 and is irradiated in a converging manner by the incoherent radiation beam S.

The object 7 is step-wise imaged by layer images by sliding a relevant hologram 53 or 53' into the beam path. The corresponding layer image is produced as a virtual image 54' in the plane of the coded image 54. Using a lens 55, the layer image can be formed as a real image on a photosensitive element 56.

The carrier disc 52 may be, for example, a photographic plate in which the various holograms are stored. The holograms may also be stored as a series on a strip-shaped photographic plate which is arranged to be displaceable in its longitudinal direction to enable positioning of the different holograms in the beam path.

What is claimed is:

1. A device for producing images of layers of a three-dimensional object from a coded image of the object, said coded image being a superposition of perspective images formed by irradiating the object from a large number of radiation source positions situated in one plane, said radiation source positions forming a distribution, said device comprising:
   illumination means for irradiating the coded image;
   a photosensitive element;
   an imaging matrix comprising a number of imaging elements equal to the number of radiation source positions, said imaging elements being situated in a matrix plane in a distribution which is the same as or linearly proportional to the distribution of radiation source positions, said imaging matrix being illuminated, via the coded image, by the illumination means to form superposed perspective images of the object on the photosensitive element, the superposed perspective images producing an image of a layer of the object on the photosensitive element; and
   means for changing the positions of the individual imaging elements in the matrix plane while maintaining the distribution of the elements linearly proportional to the distribution of radiation source positions, wherein images of different layers of the object are produced by changing the positions of the imaging elements.

2. The device of claim 1, wherein the means for changing the positions of the individual imaging elements comprises a holder capable of holding an interchangeable imaging matrix.

3. The device of claim 2, wherein the imaging elements are optical lenses.

4. The device of claim 3, wherein:
   the imaging matrix is situated at a fixed distance from, and is parallel to, the coded image; and
   the photosensitive element is arranged at a fixed distance from the imaging matrix.

5. The device of claim 4, wherein the imaging matrix has a center and comprises:
   a first flat plate for accommodating the lenses, all noncentrally located lenses being arranged in guide slots which extend radially from the matrix center; and
   means for displacing the lenses in the guide slots while maintaining the lens distribution linearly proportional to the distribution of radiation source positions.

6. The device of claim 5, wherein:
   the first plate has an axis perpendicular thereto and through the matrix center; and
   the means for displacing the lenses comprises a second plate provided on the first plate, said second plate having guide slots extending helically with respect to the matrix center, each noncentral lens being arranged in a helical guide slot, with said plate arranged so as to be rotatable with respect to the first plate around said axis.

7. The device of claim 5, wherein the means for displacing the lenses comprises a second plate provided on the first plate, said second plate having straight guide slots, with each arranged in a straight guide slot, and with said second plate arranged to be linearly displaceable with respect to the first plate.

8. The device of claim 2, wherein the imaging matrix comprises a lenticular hologram wherein each lenticule is a respective one of said imaging elements.

* * * * *

UNITED STATES PATENT AND TRADEMARK OFFICE
CERTIFICATE OF CORRECTION

PATENT NO. : 4,394,063
DATED : July 19, 1983
INVENTOR(S) : HERMANN WEISS ET AL

It is certified that error appears in the above—identified patent and that said Letters Patent is hereby corrected as shown below:

Claim 7, Line 4, after "each" insert --lens--.

Signed and Sealed this

Thirteenth Day of September 1983

[SEAL]

Attest:

GERALD J. MOSSINGHOFF

*Attesting Officer*  *Commissioner of Patents and Trademarks*